United States Patent
Bak (10) Patent No.: US 12,076,451 B2
(45) Date of Patent: *Sep. 3, 2024

(54) LIQUID FILLED LIGHT DISTRIBUTOR AND A METHOD OF USE

(71) Applicant: UV CLINICAL A/S, Hellerup (DK)

(72) Inventor: Jimmy Bak, Greve (DK)

(73) Assignee: UV CLINICAL A/S, Hellerup (DK)

(*) Notice: Subject to any disclaimer, the term of this patent is extended or adjusted under 35 U.S.C. 154(b) by 438 days.

This patent is subject to a terminal disclaimer.

(21) Appl. No.: 17/203,839

(22) Filed: Mar. 17, 2021

(65) Prior Publication Data
US 2021/0196847 A1    Jul. 1, 2021

Related U.S. Application Data (63) Continuation of application No. 14/239,159, filed as application No. PCT/DK2012/050299 on Aug. 16, 2012, now Pat. No. 10,967,080.

(30) Foreign Application Priority Data

Aug. 16, 2011 (DK) .......................... PA 2011 70447

(51) Int. Cl.
*A61L 2/10* (2006.01)

(52) U.S. Cl.
CPC ............. *A61L 2/10* (2013.01); *A61L 2202/24* (2013.01)

(58) Field of Classification Search
None
See application file for complete search history.

(56) References Cited

U.S. PATENT DOCUMENTS

| | | | |
|---|---|---|---|
| 5,228,451 | A | 7/1993 | Bales et al. |
| 5,908,415 | A | 6/1999 | Sinofsky |
| 5,997,571 | A | 12/1999 | Farr et al. |
| 6,676,656 | B2 | 1/2004 | Sinofsky |
| 2004/0039242 | A1 | 2/2004 | Tolkoff et al. |
| 2005/0031281 | A1 | 2/2005 | Nath |
| 2006/0167531 | A1 | 7/2006 | Gertner et al. |
| 2008/0159908 | A1 | 7/2008 | Redmond |
| 2011/0213339 | A1 | 9/2011 | Bak |

FOREIGN PATENT DOCUMENTS

| | | |
|---|---|---|
| EP | 2161040 A1 | 3/2010 |
| WO | 9932181 A1 | 7/1999 |
| WO | 2007095543 A2 | 8/2007 |
| WO | 2010023329 A1 | 3/2010 |
| WO | 2010097499 A1 | 9/2010 |

*Primary Examiner* — Regina M Yoo
(74) *Attorney, Agent, or Firm* — DINSMORE & SHOHL LLP

(57) ABSTRACT

The present invention relates to liquid filled light distributor comprising an elongated tubular body with a tube wall defining an in inner lumen filled with a liquid, said tubular body having
 a proximal end closed by first closing means
 a distal end closed by second closing means
Wherein the proximal end is arranged to be in optical communication with a light source and wherein the refractive index of the tube wall is n1 and the refractive index of the fluid is n2 and n1/n2<1 so that light from the light source travels along the longitudinal direction of the tubular body and that a part of the light is emitted through the tube wall along at least a part of the tubular body. Further a method of use for the liquid filled light distributor is provided.

22 Claims, 4 Drawing Sheets

LIQUID FILLED LIGHT DISTRIBUTOR AND A METHOD OF USE

CROSS-REFERENCE TO RELATED APPLICATIONS

The present application is a continuation of and claims priority to U.S. patent application Ser. No. 14/239,159, filed Feb. 17, 2014 and entitled "LIQUID FILLED LIGHT DISTRIBUTOR AND A METHOD OF USE" which is a US National Phase of PCT/DK2012/050299, filed Aug. 16, 2012, which claims priority to Danish Patent Application No. PA 2011 70447, filed Aug. 16, 2011, which is incorporated by reference herein in its entirety.

FIELD OF INVENTION

The present invention relates to a liquid filled light distributor comprising an elongated tubular body with a proximal end and a distal end. The invention further relates to a method for disinfecting the inner lumen of a hollow body by use of the liquid filled light distributor according to the present invention.

BACKGROUND OF INVENTION

Elongated lights sources emitting UV light e.g. from diodes and the use of the light sources to disinfect lumens in medical devices are known from e.g. US 2007/0187626. However these devices have significant drawbacks, which render them impractical and inefficient in use. For example the known sources needs to be rotated in order to be able to submit an entire area of an inner wall of a lumen to disinfecting UV light as the UV sources are point sources with limited emission angle and area.

Besides the difficulties of placing the diodes inside narrow cavities/lumens electrical wiring through the length of the elongated light source is needed. If the light source is used in wet or damp conditions or for medical purposes in relation to a human body, the electrical wiring, possibly in-vivo is a challenge. E.g. patient safety can be jeopardized because even small currents and voltage can be mortal. In addition, maintenance is much easier if the electrical powered light sources are ex-vivo and not in direct contact with the medical device.

Thus there is a need for an elongated light source emitting light continuously along the length and homogeneously around the circumference of the light source while at the same time being safe and practical in use.

SUMMARY OF INVENTION

In a first aspect of the present invention as defined in the opening paragraph is provided a liquid filled light distributor which is arranged to emit light, especially UV light, over at least a part of the length of the liquid filled light distributor in a 360° radial distribution In a second aspect of the present invention is provided a liquid filled light distributor which is bendable In a third aspect of the present invention is provided a liquid filled light distributor which relies on non-hazardous materials In a fourth aspect of the present invention is provided a liquid filled light distributor which relies at least partly on low cost materials In a fifth aspect of the present invention is provided a liquid filled light distributor which allows a simple manufacturing process In a sixth aspect of the present invention is provided a liquid filled light distributor which enables control of the amount and direction of the emitted light In a seventh aspect of the present invention is provided a liquid filled light distributor without a source of electricity inside the light distributor.

In an eighth aspect of the present invention is provided a liquid filled light distributor which is disposable.

In an ninth aspect of the present invention is provided a method which allows disinfection if the inner lumen of a hollow body

DESCRIPTION OF THE INVENTION

These and other aspects and advantages are achieved by a liquid filled light distributor comprising an elongated tubular body with a tube wall defining an in inner lumen filled with a liquid, said tubular body having a proximal end closed by first closing means a distal end closed by second closing means Wherein the proximal end is arranged to be in optical communication with a light source and wherein the refractive index of the tube wall is n2 and the refractive index of the fluid is n1 and $n2/n1<1$. So that light from the light source propagates along the longitudinal direction of the tubular body and that a part of the light is transmitted through the tube wall along at least a part of the tubular body, which thus constitutes a versatile light source which can be inserted in narrow passages.

The refractive index of the fluid and the refractive index of the tube wall of the tubular body is chosen to ensure that light propagates in the longitudinal direction of the tube (i.e. from the proximal end to towards the distal end) as well as it is ensured that at least part of the light is emitted through the tube wall along at least a part of the tubular body. Herby, the light distributor is effective in delivering light not only at the distal end but also radially along the length of the tubular body.

When the liquid filled light distributor is connected to a light source at the proximal end, light is emitted into the liquid in the lumen of the tubular body. From here the light will propagate towards the distal end of the liquid filled light distributor.

Whereas light theoretically under special conditions may be described as propagating in parallel with no scattering in either liquid or internal tube surfaces, this is not the case under actual circumstances. The light will enter the lumen of the tubular body with a certain spread on the propagation angle which means that light will travel towards the distal end and that part of the light will be propagating at angles different to the parallel case. When propagating light reach the tube wall it may be reflected and/or transmitted through the tube wall (refracted) depending on the relative characteristics of liquid and tube wall. It may also be absorbed in the tube wall depending on wall absorption and wall thickness.

One parameter determining the ratio between reflected and transmitted light is the relative refractive index of fluid and tube wall. In cases where $n2/n1<1$, i.e. as in the present case where the refractive index of the liquid is higher than the refractive index of the tube wall, a critical angle exists beyond which all light will be reflected on the inner side of the tube wall. The critical angle is determined by Snells law. See FIG. 7. This means that by selecting the relative refractive index n2/n1 to be lower than 1 it is possible to optimize the amount of light which stays inside the lumen of the tubular body. This is as described above due to the fact that the part of the light impinging the tube wall with an angle over the critical angle it is completely reflected and thereby stays inside the lumen of the tubular body and may continue to propagate towards the distal end.

By changing the relative refractive index between liquid and tube wall, i.e. by changing the ratio n2/n1, the ratio between how much light is emitted out through the tube wall and how much light stays and propagates inside the inner lumen of the tubular body is changed.

The proximal end can be arranged to be in optical communication with a light source in numerous ways. E.g. the proximal end may have a simple form for simply fitting into a light source or into a connector piece. Alternatively the proximal end may be arranged with means such as protrusions, guides, tread for securing directly to the light source via one or more connector pieces.

The second closing means of the distal end may be e.g. a film, cap, clamp or similar or even simply be a glued, pressed and/or welded part of the tubular body.

The first closing means may be e.g. film, glass, quartz and/or an element with selected optical properties for guiding, collecting, angling, transmitting etc. the light from the light source.

The first closing means may in some embodiments form part of an arrangement for connection and optical communication with the light source.

In some embodiments the refractive indices of the material that can be used for the tube wall of the light distributor are chosen to be lower than 1.33 (1.33 is the refractive index of water). If the fluid inside the light distributor is water and an ionic compound is added to the water it is possible to increase the refractive index of the liquid up to e.g. ~1.37. Some polymers (for example teflons) can have a refractive index as low as 1.29-1.31. Because the proportion of light that is transmitted depends on the difference in refractive index between the wall and liquid it is advantageous to have a large span between the two indices (n1 and n2).

Ratios n2/n1 may for example be chosen in the interval: 0.94 (e.g. 1.31/1.33)-0.98 (e.g. 1.29/1.37).

In order to obtain a sufficient emission of light through the tube wall along at least part of the tubular body the ratio n2/n1 must preferably be <0.98 or even lover e.g. <0.96. This is due to the fact that if the ratio becomes too high the liquid light guide will lead all light to the distal end of the tubular body with no or very limited transmission of light through the tube wall along the length of the tubular body.

The transmittance (fraction of light transmitted) through the wall depends on the absorption properties of the wall material and its thickness. The transmittance is therefore the same along the entire length of the light distributor and consequently the same fraction of light propagating along the inner space of the light distributor is emitted to the surroundings. In order to achieve an even light emission as possible along the entire length of the light distributor it may be important to guide the light to the distal as effectively as possible. This can be achieved by decreasing the ratio n2/n1 i.e. optimizing the light propagating properties of the light distributor.

Thus, as clear from the above, by changing the relative refractive index n2/n1 of liquid and tube wall it is possible to change the amount of light which propagates all the way through the tubular body to reach the distal end and the amount of light emitted radially from the tubular body.

Preferably 20-80% of the light is left at the distal end so that light is emitted through the tube wall along the full length of the tubular body but in a ratio which allows part of the light to be left inside the tubular body at the distal end. If 50-70% of the light is left at the distal end the minimal light flux through the tube wall at the distal end may be in an ideal range. However, the percentage of light left at the distal ends depends on the length of the liquid filled light distributor. Thus, the interval 50-70% may for example relate to the case of a 10-30 cm long liquid filled light distributor. If 100% light is left at the distal end no light has escaped though the tube wall. If 0% is left all light has escaped through the tube wall (and/or has been lost to absorption and similar effects) before reaching the distal end of the light distributor.

If the light distributor is short a relatively high ratio n2/n1 may be used. If the light distributor is long it becomes more important to have a lower ratio in order to have light left inside the light distributor at the distal end.

The attenuation of light inside the light distributor follows an exponential decay curve. In order to reduce the decay rate the transmittance through the tubular body from the proximal to the distal end should be increased. This can be achieved by decreasing the ratio of the refractive indices such that the critical angle increases and light from more angles are reflected to the distal end.

If the liquid is a saline solution the liquid filled light distributor according to the invention can be safe to use and manufacture, as well as the liquid used is cheap, easy to acquire and easy to dispose of. Further advantages are that saline liquid transmits light over a wide range of wave lengths including UV light, and advantageously including UVC light.

A solution made with a pure salt (e.g. NaCl) provides a liquid with no or an insignificant number of impurities, which will help minimize unwanted scattering and/or absorption of the light caused by the liquid inside the tubular body.

Generally even if the fluid is not a saline solution it can be an advantage to use pure salts and fluids with a minimum of particles or other substances which may absorb or scatter light for making the liquid to fill the light distributor.

Many ionic solutions are transparent in the UVC region. They will increase the refractive index of the solution compared to pure water (1.33 in the visible region) and could in principle be used. Solutions based on NaCl, however, are cheap and non-poisonous which is relevant e.g. if there should be a leak when inserted into a medical device.

By controlling the salinity of the liquid it is possible to control the refractive index of the liquid, which is one of the significant parameters determining the amount of light emitted through the tube wall and the amount of light propagating from the proximal end to arrive at the distal end of the liquid filled light distributor. Salt concentration of the saline solution may be at least 10 g/100 ml, at least 20 g/100 ml or even 30 g/100 ml or higher. The refractive index of the saline solution depends on the salt concentration in that the refractive index of the saline solution is increased when the salt concentration is increased.

From CRC chemical handbook we can make a table that give the refractive indices for different NaCl solutions (and others as well). For instance:

0% (pure water)=1.33
5%=1.34
10%=1.35
20%=1.37
26%=1.38

For visual light, however these factors are also applicable in the case of UV light.

Dupont's AF Teflon: 1.29
FEP teflons: ~1.30-1.31
PTFE teflons ~1.30-1.33

The refractive index of the liquid can be adjustable by simple means e.g. by changing the concentration of a content such as a salt.

If other liquids than saline are used they are preferably chosen to have a high transmission in relevant wave length ranges, e.g. with a high transmission of UVC light, chosen to have a low amount of impurities in order not to absorb and disperse the light propagating in the lumen of the tubular body, be non-hazardous and/or cheap. Also used liquids must satisfy the requirements to refractive index relevant to embodiments of the invention. The refractive index of the liquid can be adjustable by simple means e.g. by changing the concentration.

In order to obtain a reasonable even light distribution along the length of the light distributor the transmission through the light distributor may in many embodiments preferably be as high as possible. The fraction 'f' of light emitted (or transmitted) through the wall at a distance 'L' from the light source is the same as the fraction emitted at 'L+x'. If the light intensity 'I' is strongly attenuated close to the light source only a small part will be emitted in the distal end: I(L+x)*f. If the light that reaches the distal end can be back reflected an even more even emission from the light source may be accomplished.

In several preferred embodiments the distal end is coated with a reflective material. By coating the distal end with a reflective material or otherwise providing a reflective material to the distal end of the lumen of the tubular element and/or to the second closing means, light which has propagated from the proximal end to the distal end will be reflected back through the liquid in the lumen of the tubular body towards the proximal end.

Reflective materials may include different kinds of film or coating of one or more metals such as a silver coating or more preferable an aluminum coating as this scan provide a very high reflectivity.

The reflection of the light back through the liquid filled light distributor means that the overall transmission through the tube walls may be increased. Also it means that it is possible to use the liquid filled light distributor as a light source in a channel wherein it is desired to subject the walls of the channel to light while at the same time preventing light escaping through the end of the channel, as light is only emitted radially from the tubular body and not through the distal end itself or and/or through the second closing means.

The liquid filled light distributor may also be arranged with a reflective material in other regions where it is preferred to avoid emission of light and from where it is advantageous that light is reflected to stay inside the lumen of the tubular body of the light distributor. The reflective material may be permanent or removable e.g. in the form of a removable sleeve.

Advantageously the material and/or thickness of the tube wall may be selected to optimize the desired properties of the liquid filled light distributor of the present invention. A liquid filled light distributor can also comprise a tubular body made of more than one material and/or with one or more wall thicknesses.

Thus, the material(s) may be chosen to have a refractive index which helps provide a desired n1/n2 ratio as well as the wall thickness may be chosen in order to achieve desired transmission properties of light through the tube wall.

Preferably the material of the tube wall has a thickness of less than 0.15 mm, preferably less that 0.10 mm or even down to 0.05 mm or less as this may ensure specific mechanical properties while keeping the amount of light lost to absorption in the tube wall at a minimum.

If the tube wall is too thick too much light may be absorbed by the material of the tube wall.

If the tube wall is too thin the strength of the tube wall may be compromised. The ability to provide a thin tube wall depends on the type of material chosen for the tube wall.

Preferred tube wall materials includes: Teflon such as Fluorinated ethylene propylene (FEP), polytetrafluoroethylene (PTFE), amorphous fluoropolymers (AF) as they have low refractive indices. Different types of folios and thin sheets of polymers may also be highly transparent to UV and preferably to UV C light and thus be usable for use in the present invention.

By mechanical properties are meant e.g. strength, flexibility, shear strength, transmission, impermeability to the given liquids inside the inner lumen etc.

It may also be advantageous to manufacture the tube wall in a material which makes it possible to obtain a smooth inner surface of the tube wall as this will minimize the scattering of the light reflected off the tube wall inside the lumen.

In preferred embodiments the proximal end is arranged with a connector piece which allows easy connection to a light source. Preferably the connector piece is arranged to minimize the loss of light from the light source. I.e. the connector piece may be arranged not to hinder the transmission of light from the light source to the proximal end of the liquid filled light distributor of the present invention.

The connector piece can in various embodiments be e.g. luer locks, different type of locks which "clicks" together, unions or other threaded lock systems.

In further preferred embodiments, the tubular body is flexible as this allows the insertion of the liquid filled light distributor in lumens, passages, channels etc. which may be bend or otherwise have obstacles which will prevent the insertion of a rigid liquid filled light distributor.

Light source used together with the liquid filled light distributor can for example be UV diodes (LEDs), visible LEDs, laser light sources, bulbs with or without optics etc.

Alternatively the light source may comprise a light guide such as an optical fibre whereto the light distributor according to the present invention can be connected. Hereby a wider span is achieved making e.g. in vivo diagnostics possible in areas which otherwise may be hardly assessed. Also the options for Photo dynamic Therapy (PDT) will be increased due to the wide range in which the optical fibre in connection with the light distributor according to the present invention may be effectively operated offering unique options to reach and treat otherwise hard to reach areas.

In several embodiments the light distributor comprises one or more transmitting fields. These transmitting fields are preferably made of one or more materials which transmits lights and which does not guide the light. For example such transmitting fields may be of COC polymer materials or other materials with a refractive index chosen depending on the refractive index of the fluid inside the light distributor to ensure that light is transmitted through the transmitting field. This also means that in advantageous embodiments the material of the transmitting field does not guide the light inside the liquid light distributor but lets it escape through the transmitting field. Transmitting fields may thus function as a transparent window through which more light is emitted from the liquid filled light distributor than from the rest of the light distributor.

The transmitting fields can be an integrated or added part of the liquid filled light distributor arranged in selected areas or e.g. the transmitting fields can be a tube section or end piece optionally functioning as the second closing means. If the diameter of such a tube section or end piece is selected to be different from the general diameter of the liquid filled light distributor specific illumination properties can be achieved. For example the diameter of a transmitting field in form of an end piece can be larger than the diameter of the main part of the liquid light distributor and thus function as a more intense light source compared to the light emitted from the rest of the liquid filled light distributor.

Preferably the light source is a UV C source as UV C light is effective as a disinfecting agent. This also means that mentioned UV transmitting materials is preferably transmitting UV C light with a minimum loss.

If the tube wall is transparent to UV light many advantageous embodiments may be achieved wherein this special property is utilized.

The properties of the UV light are further enhanced if the first closing means is a UV transparent film as this means that UV light from the light source connected to the tubular light source by the proximal end is allowed to pass into the lumen of the tubular light source.

Alternative light transmitting and especially UV light transmitting materials may be used for the first closing means.

In several embodiments the liquid filled light distributor is arranged with parts which is intended and suited for single use only. I.e. the liquid filled light distributor can be disposable.

For a disposable liquid filled light distributor it may be advantageous that the different parts such as tube wall, connectors, closing means and/or liquid are chosen to be cheap and/or non-toxic.

The properties of the liquid, tube wall and first closing means, which allows the propagation and emission of UV light provides a number of important abilities to the liquid filled light distributor according to the present invention.

Thus, according to the present invention a versatile liquid filled light distributor is achieved and especially a liquid filled light distributor which may be used to disinfect hard to reach places and narrow channels are provided.

The inventors of the present invention have surprisingly shown that the emission through the tube wall which is considered unfavourable side effect and imperfection in other setups known from traditional light guides is in fact a useful and tuneable feature which can be utilized with great advantages.

For example a liquid filled light distributor according to the present invention can be used to disinfect the inner channel of a device. UV light is known for its germicidal properties and the present invention when used to distribute, emit and guide UV light may advantageously be used to disinfect hard to reach places inside e.g. a channel in an object. The fact that light can be emitted radially along the full length of the tubular body of the present invention means that e.g. a channel can be completely subjected to UV light by use of the present invention. The present invention can even be used without the need to turn or otherwise reposition the liquid filled light distributor during use.

The present invention can also be used to e.g. UV hardening of materials such as plastics or glues in situations where known UV light guides may be less applicable as they only emit light at the end. Also the present invention can be used as an alternative light source with or without UV light in conditions which require insertion in narrow, wet and/or damp spaces and where the light distributing properties of the liquid filled light distributor according to the present invention may be useful.

Especially advantageously the liquid filled light distributor can be used to disinfect the inner channel of a medical device such as an EndoTracheal Tube (ETT) before and/or during use. Depending on how the refractive indexes n1 and n2 are chosen the tubular liquid filled light distributor can be configured to disinfect the full length of a channel by allowing UV light to be emitted though the full length of the light distributor. Preferably n1 and n2 are chosen in order to have a 40-70% light left in the lumen at the distal end in order to achieve a high transmission of UV light through the tube wall at the distal end.

When the present invention is used the lights source can be placed outside the human body in medical applications and then avoid the need for in vivo placement of electrical wires as it would be required if an elongated light source with LEDs as previously known was used.

The fact that no electrical installations or other type of charges are required inside the light distributor according to the present invention also allows the use of the present invention as a light source in spaces filled with combustible materials as gases or fluids. This offers a safe alternative to other more traditional lights sources also under these demanding conditions.

It is also possible that the transmission of UV light through the tube wall along at least a part of the tubular body and/or at the distal end is adjusted (by selecting appropriate n2/n1 ratio, materials and tube wall thickness) in order to keep a device sterile. This is for example relevant if the liquid filled light distributor according to the present invention is inserted into a sterile lumen in a device and is operated over prolonged time in order to maintain the inner lumen of the device in a disinfected state.

The liquid filled light distributor can be permanently or removeably inserted into the device in which it is used. It is also possible that the liquid filled light distributor can be an integrated part of a device e.g. a medical device.

The advantages of the present invention are also achieved by a method of disinfecting the inner lumen of a hollow body at least comprising the steps of Acquiring a liquid filled light distributor
Connecting the liquid filled light distributor with a tubular body to a UV source
Inserting the liquid filled light distributor with a tubular body into the inner lumen of the hollow body
Submitting the inner lumen of the hollow body to UV light via the liquid filled light distributor with a tubular body for a period of time Preferably the liquid filled light distributor used in the method is a liquid filled light distributor according to the present invention and thus the method may provide all the advantages and possibilities described in the previous sections.

The method according to the present invention is especially useful if the hollow body is a medical device The method can even be used if the medical device is operational during the sterilization process. This can for example be in the case where a ETT in a patient is kept sterile by use of the present invention. In this case it is especially advantageous if the distal end and/or second closing means is provided with a reflective material as this will ensure that only the inner lumen of the ETT receives the UV light and that no UV light reaches any parts of the patient.

DESCRIPTION OF DRAWINGS

FIG. 1 shows a liquid filled light distributor according to the present invention before insertion in a connector piece.

DETAILED DESCRIPTION OF THE INVENTION

FIG. 1 shows a liquid filled light distributor 1 with an elongated tubular body 2. The liquid filled light distributor 1 has a proximal end 3 with an opposing distal end 4. The proximal end 3 is closed with a first closing means 5 and the distal end is closed with second closing means (not shown) thus an inner lumen (not shown) is formed along the full length of the liquid filled light distributor 1.

Figures 2, 3, 4:
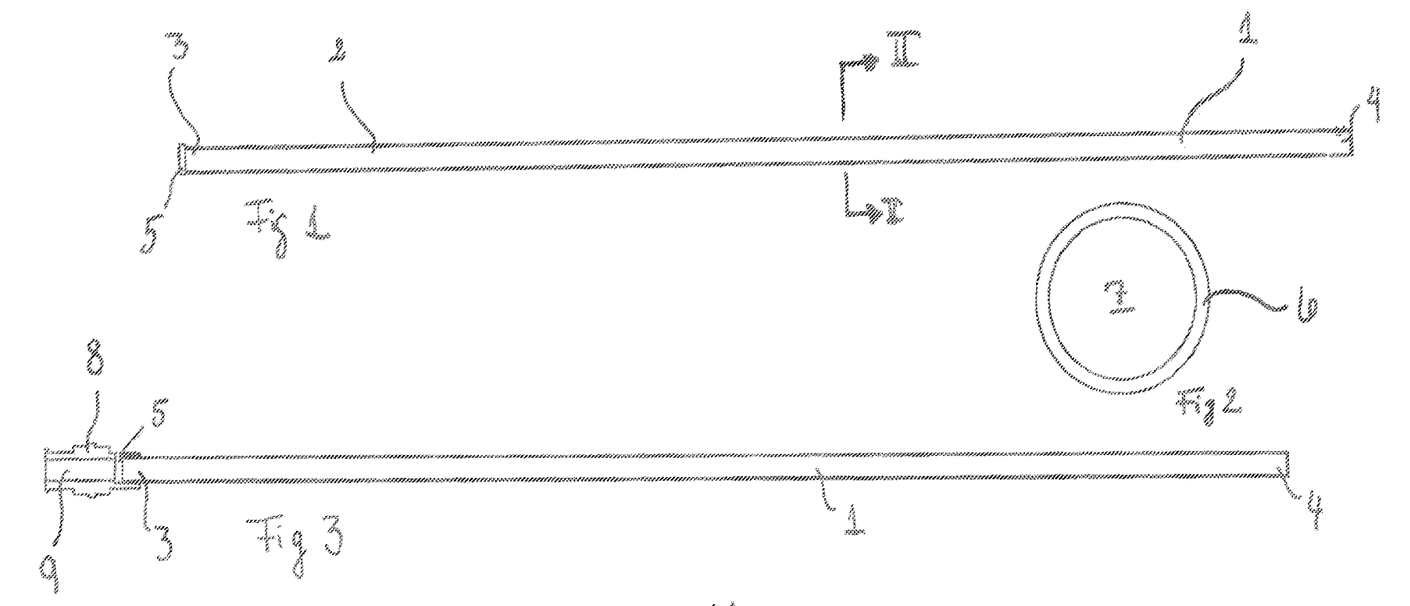
FIG. 2 shows an enlarged cross section taken along the line II-II indicated in FIG. 1
FIG. 3 shows the liquid filled light distributor known from FIG. 1 arranged with the connector piece
FIG. 4 shows the liquid filled light distributor from FIGS. 1 and 2 together with and light source and an additional connection

In FIG. 2 is shown an enlarged cross section as indicated in FIG. 1 the elongated tubular body 2. The elongated tubular body has a tube wall 6 around an inner lumen 7.

FIG. 3 shows the liquid filled light distributor 1 known from FIGS. 1 and 2 inserted in a connector piece 8. The liquid filled light distributor 1 may be fixatedly or releasably connected to the connector piece 8. The connector piece 8 has a through going bore 9 allowing optical communication with a light source (not shown).

FIG. 4 shows the liquid filled light distributor 1 with the connector piece 8 ready to be connected to a light source 10 via an intermediate connector 11. In this embodiment the light source comprises a LED 12 in a housing 13. The housing 13 has a threaded part 14 for connecting to the intermediate connector 11. The intermediate connector has a first part 15 for receiving the housing 13 of the light source 10 and a second part for receiving part of the connector piece 8 on the liquid filled light distributor 1.

When the liquid filled light distributor 1 is connected to the light source 10, light will propagate through the liquid along the length direction of the liquid filled light distributor 1 i.e. along the longitudinal direction of the tubular body. On the way towards the distal end of the liquid filled light distributor 1, part of the light will be emitted through the tube wall 6.

Figure 5:
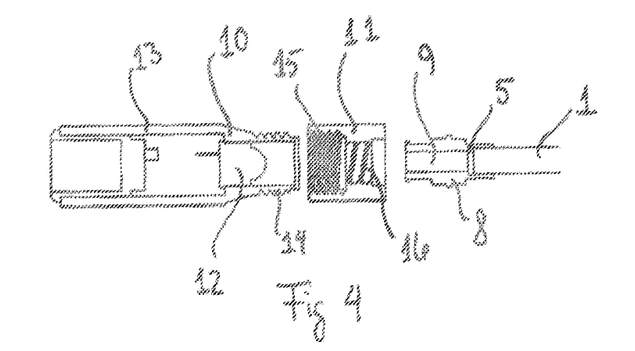
FIGS. 5a and 5b illustrates different configurations of reflective material applied to the liquid filled light distributor
FIGS. 5c and 5d illustrates different configurations of transmitting fields
Figure 5A:
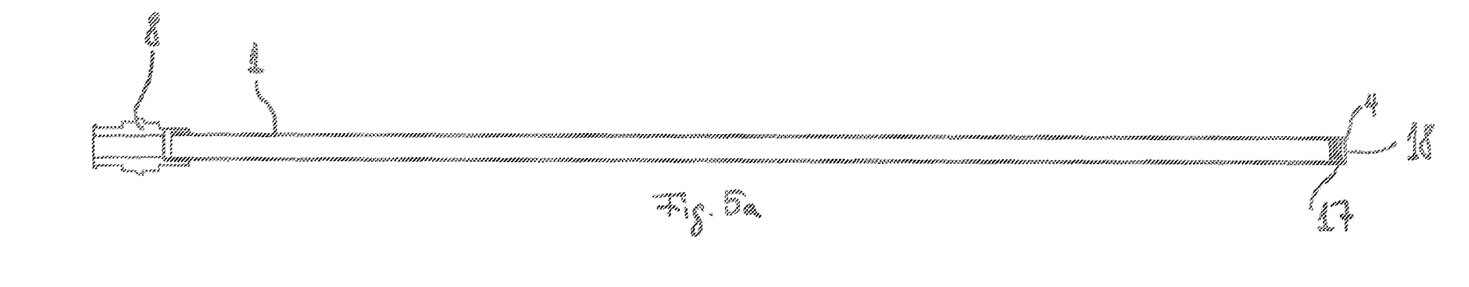
Figure 5B:
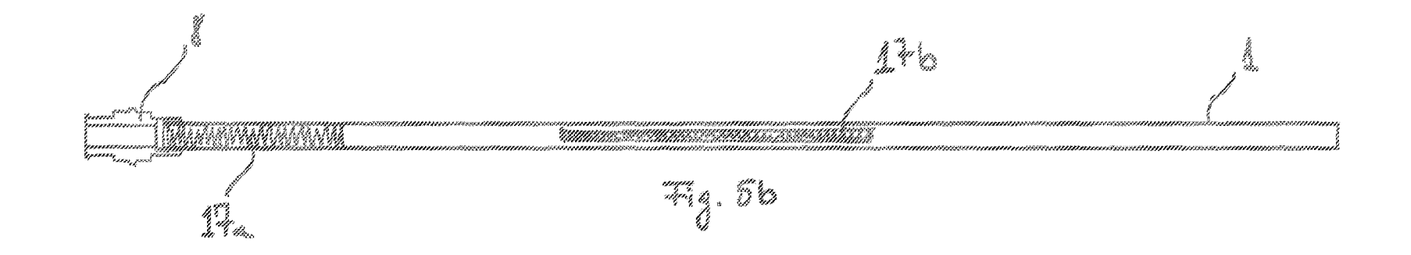

FIG. 5a shows a liquid filled light distributor 1 as known from the previous figures with a reflective material 17 applied at the distal end 4. In the shown embodiment the reflective material extends onto the tube wall 6 in an area close to the very tip of the liquid filled light distributor 1. In other embodiments (not shown) the reflective material can be applied onto only the end surface 18 if desired. FIG. 5b shows how reflective material can be applied in other areas of the tube wall of the elongated body in order to direct and limit the emitted light from the liquid filled light distributor 1 to specific areas. The reflective material can cover e.g. larger circumferential areas as illustrated by the area 17a near the connector piece 8 and/or it may form stripes 17b along the length direction of the liquid filled light distributor 1.

Figure 5C:
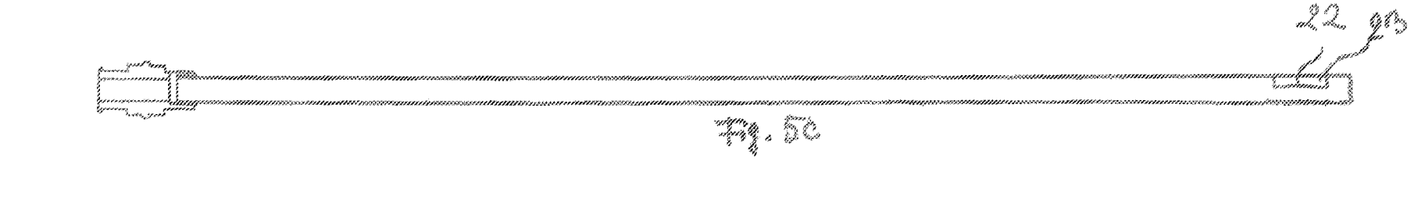
Figure 5D:
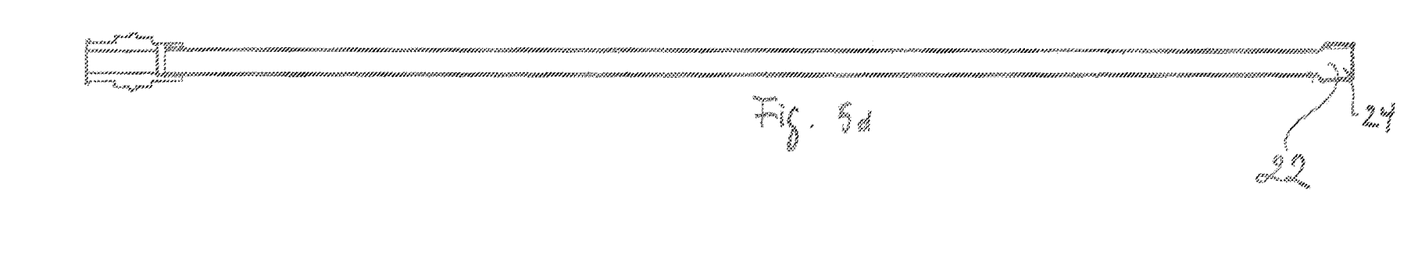

FIGS. 5c and 5d shows examples of liquid filled light distributors comprising transmitting fields 22 in areas selected to enable higher transmission of light in specific areas. In FIG. 5c the light transmitting field 22 is a rectangular window 23 arranged near the distal end of the light distributor. In FIG. 5d the light transmitting field 22 is formed by an end piece 24 with a larger diameter than the main part of the light distributor.

Figure 6A:
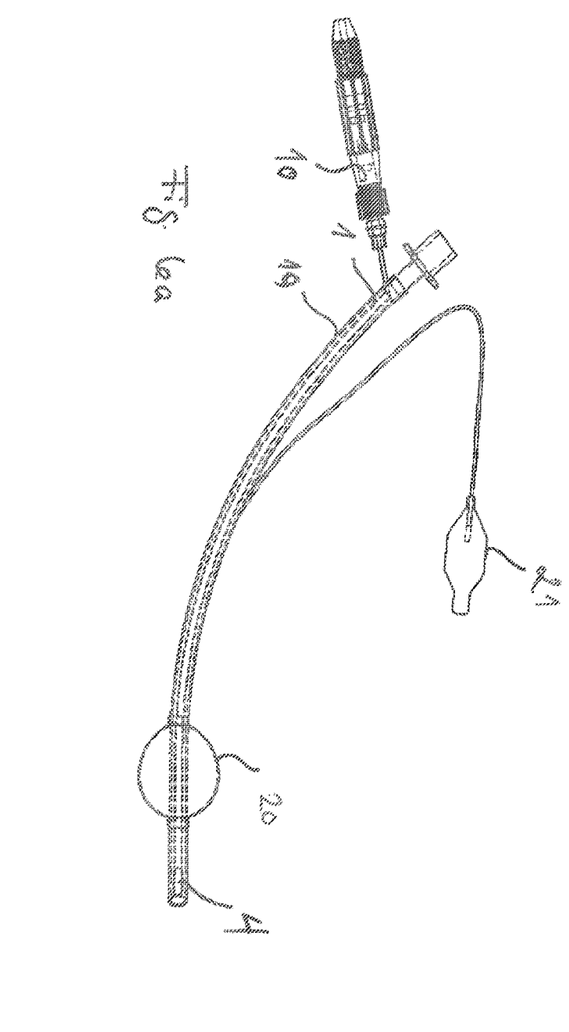
FIGS. 6a and 6b show the use of a liquid filled light distributor in an ETT
Figure 6B:
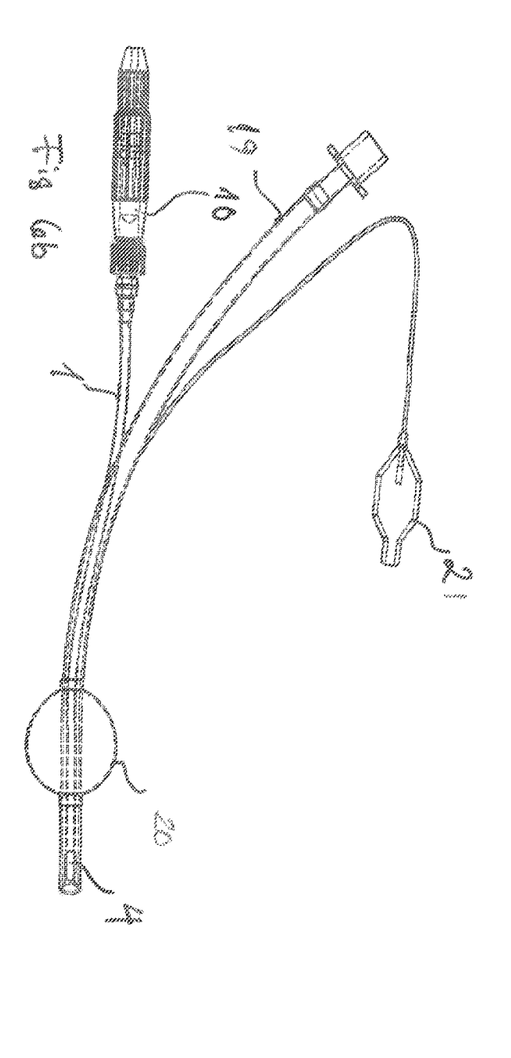

FIG. 6a and FIG. 6b show examples of light distributers 1 according to the present invention used to illuminate and hereby help minimize the contamination of the inside of an ET tube 18. The ET tube is arranged with a balloon cuff 19 and a device 20 for inflating the cuff 19. In the FIGS. 6a and 6b the part of the liquid filled light distributor which is inside the ET tube is illustrated with broken lines.

FIG. 6a show an exemplary arrangement wherein the light distributor according to the present invention is arranged to illuminate the full length of the ET tube 18.

In FIG. 6b the light distributor according to the present invention is introduced into the ET tube closer to the distal end of the ET tube and is thus arranged to illuminate a shorter part of the ET tube.

As described earlier the light distributor according to the present invention can be arranged as a separate part for introduction into the ET tube or it may be completely or partly integrated into the ET tube e.g. during manufacturing of the ET tube.

Figure 7:
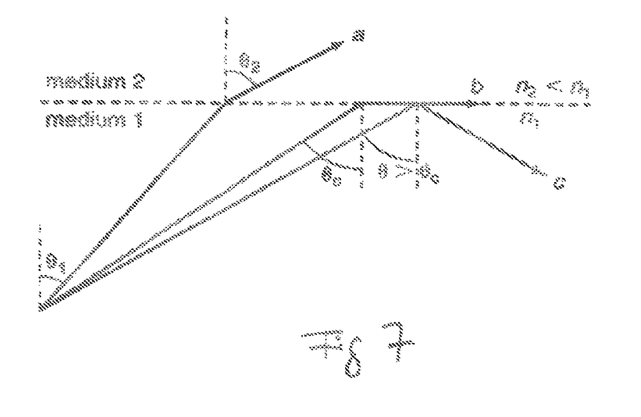
FIG. 7 illustrates refraction, critical angle and light propagation in the liquid filled light distributor.

FIG. 7 illustrates how light with different propagation angles $\Theta_1$ from a light source will be refracted as illustrated by arrow a or reflected as illustrated by arrow c at a surface between two mediums. The refraction and reflection depends on whether the light impinges the surface at an angle lower or higher than the critical angle $\Theta_c$.

The invention claimed is:

1. A UV light disinfection device comprising a flexible elongated tubular body with closed ends, the flexible elongated tubular body comprising:
   a tube wall having a refractive index n2, wherein the tube wall is transparent to ultraviolet (UV) light;
   a proximal end closed by a first closure;
   a connector piece arranged on the proximal end and abutting the first closure;
   a housing comprising a UV light source for providing UV light, wherein the housing is releasably connected to the connector piece;
   a distal end closed by a second closure joined with the flexible elongated tubular body; wherein the tube wall, the first closure, and the second closure define a closed inner lumen along the full length of the flexible elongated tubular body; and
   a liquid contained within the closed inner lumen between the first closure and the second closure such that the liquid is retained within the closed inner lumen, the liquid having a refractive index n1,
   wherein n2/n1<1 so that the UV light disinfection device is configured for guiding UV light from the light source inside the liquid filled inner lumen along a longitudinal direction of the flexible elongated tubular body, wherein a part of the UV light is emitted through the tube wall, such that the UV light disinfection device is configured for emitting UV light radially from and along the length of the flexible elongated tubular body.

2. The UV light disinfection device of claim 1, wherein the liquid is a transparent ionic solution.

3. The UV light disinfection device of claim 2, wherein the transparent ionic solution is a saline solution and a salt concentration of the saline solution is at least 10 g/100 ml, or at least 20 g/100 ml, or at least 30 g/100 ml.

4. The UV light disinfection device of claim 1, wherein n2/n1<0.98.

5. The UV light disinfection device of claim 1, wherein n2/n1<0.96.

6. The UV light disinfection device of claim 1, wherein the second closure is joined with the flexible elongated tubular body such that the second closure is a glued, pressed and/or welded part of the flexible elongated tubular body.

7. The UV light disinfection device of claim 1, wherein the distal end of the closed inner lumen is provided with a reflective material such that light which has propagated from the proximal end to the distal end of the closed inner lumen will be reflected back through the liquid in the closed inner lumen of the flexible elongated tubular body towards the proximal end.

8. The UV light disinfection device of claim 7, wherein the reflective material is selected from the group of metals, including silver and aluminum, or a combination thereof.

9. The UV light disinfection device of claim 1, wherein the second closure and the distal end of the closed inner lumen are non-transparent such that no UV light can exit the inner lumen through the distal end.

10. The UV light disinfection device of claim 1, wherein the inner surface of the tube wall is smooth to minimize the scattering of light reflected off the tube wall inside the closed inner lumen.

11. The UV light disinfection device of claim 1, wherein the material of the tube wall is selected from the group of: Teflon, Fluorinated ethylene propylene (FEP), polytetrafluoroethylene (PTFE), and amorphous fluoropolymers (AF).

12. The UV light disinfection device of claim 1, wherein the ratio n2/n1 and the distance between the proximal end and distal end are configured such that 20-70% of the light is left at the distal end, or 40-60% of the light is left at the distal end.

13. The UV light disinfection device of claim 1, wherein the first closure is a UV transparent material.

14. The UV light disinfection device of claim 1, comprising one or more transmitting fields preferably arranged near or as part of the distal end and/or the second closure.

15. The UV light disinfection device of claim 1, wherein the connector piece comprises a through going bore for allowing the UV light to pass through the through going bore.

16. The UV light disinfection device of claim 1, wherein the housing is releasably connected to the connector piece via an intermediate connector between the housing and the connector piece.

17. The UV light disinfection device of claim 1, wherein the UV light source comprises a UV light emitting diode (UV-LED) for providing the UV light.

18. A UV light disinfection device comprising a flexible elongated tubular body with closed ends, the flexible elongated tubular body comprising:
a tube wall having a refractive index n2, wherein the tube wall is transparent to ultraviolet (UV) light;
a proximal end closed by a first closure;
a distal end closed by a second closure joined with the flexible elongated tubular body such that the second closure is a glued, pressed and/or welded part of the flexible elongated tubular body; wherein the tube wall, the first closure, and the second closure define a closed inner lumen along the full length of the flexible elongated tubular body; and
a liquid contained within the closed inner lumen between the first closure and the second closure such that the liquid is retained within the closed inner lumen, the liquid having a refractive index n1,
wherein n2/n1<1 so that the UV light disinfection device is configured for guiding UV light inside the liquid filled inner lumen along a longitudinal direction of the flexible elongated tubular body, wherein a part of the UV light is emitted through the tube wall, such that the UV light disinfection device is configured for emitting UV light radially from and along the length of the flexible elongated tubular body.

19. A UV light disinfection device comprising a flexible elongated tubular body with closed ends, the flexible elongated tubular body comprising:
a tube wall having a refractive index n2, wherein the tube wall is transparent to ultraviolet (UV) light;
a proximal end closed by a first closure;
a distal end closed by a second closure joined with the flexible elongated tubular body; wherein the tube wall, the first closure, and the second closure define a closed inner lumen along the full length of the flexible elongated tubular body and wherein the second closure is non-transparent such that UV light cannot exit the closed inner lumen through the second closure, and
a liquid contained within the closed inner lumen between the first closure and the second closure such that the liquid is retained within the closed inner lumen, the liquid having a refractive index n1,
wherein n2/n1<1 so that the UV light disinfection device is configured for guiding UV light inside the liquid filled inner lumen along a longitudinal direction of the flexible elongated tubular body, wherein a part of the UV light is emitted through the tube wall, such that the UV light disinfection device is configured for emitting UV light radially from and along the length of the flexible elongated tubular body.

20. A UV light disinfection device comprising a flexible elongated tubular body with closed ends, the flexible elongated tubular body comprising:
a tube wall having a refractive index n2, wherein the tube wall is transparent to ultraviolet (UV) light;
a proximal end closed by a first closure;
a distal end closed by a second closure joined with the flexible elongated tubular body; wherein the tube wall, the first closure, and the second closure define a closed inner lumen along the full length of the flexible elongated tubular body, wherein the inner surface of the tube wall is smooth to minimize the scattering of light reflected off the tube wall inside the closed inner lumen, and
a liquid contained within the closed inner lumen between the first closure and the second closure such that the liquid is retained within the closed inner lumen, the liquid having a refractive index n1,
wherein n2/n1<1 so that the UV light disinfection device is configured for guiding UV light inside the liquid filled inner lumen along a longitudinal direction of the flexible elongated tubular body, wherein a part of the UV light is emitted through the tube wall, such that the UV light disinfection device is configured for emitting UV light radially from and along the length of the flexible elongated tubular body.

21. A method of disinfecting the inner lumen of a hollow body of a medical device, the method at least comprising the steps of:
   providing a UV light disinfection device including,
   a flexible elongated tubular body with closed ends, the flexible elongated tubular body comprising:
   a tube wall having a refractive index n2, wherein the tube wall is transparent to ultraviolet (UV) light;
   a proximal end closed by a first closure;
   a distal end closed by a second closure joined with the flexible elongated tubular body; wherein the tube wall, the first closure, and the second closure define a closed inner lumen along the full length of the flexible elongated tubular body; and
   a liquid contained within the closed inner lumen between the first closure and the second closure such that the liquid is retained within the closed inner lumen, the liquid having a refractive index n1, wherein n2/n1<1 so that the UV light disinfection device is configured for guiding UV light inside the liquid filled inner lumen along a longitudinal direction of the flexible elongated tubular body, wherein a part of the UV light is emitted through the tube wall, such that the UV light disinfection device is configured for emitting UV light radially from and along the length of the flexible elongated tubular body;
   connecting the UV light disinfection device with the flexible elongated tubular body to a UV source,
   inserting the UV light disinfection device with the flexible elongated tubular body into the inner lumen of the hollow body of the medical device, and
   submitting the inner lumen of the hollow body of the medical device to UV light via the UV light disinfection device with the flexible elongated tubular body for a period of time,
   wherein the medical device is operational during sterilization.

22. The method according to claim 21, wherein the medical device is an EndoTracheal Tube (ETT).

* * * * *